United States Patent
Möller et al.

(10) Patent No.: US 6,472,395 B1
(45) Date of Patent: Oct. 29, 2002

(54) AGENT FOR USE IN TRANSPLANTATION (75) Inventors: Lennart Möller, Älvsjö (SE); Jan Bergman, Spånga (SE)

(73) Assignee: Leif J. I. Lundblad, Stockholm (SE)

( * ) Notice: Subject to any disclaimer, the term of this patent is extended or adjusted under 35 U.S.C. 154(b) by 0 days.

(21) Appl. No.: 09/914,300

(22) PCT Filed: Feb. 18, 2000

(86) PCT No.: PCT/SE00/00339

§ 371 (c)(1),
(2), (4) Date: Dec. 3, 2001

(87) PCT Pub. No.: WO00/50039

PCT Pub. Date: Aug. 31, 2000

(30) Foreign Application Priority Data

Feb. 25, 1999 (SE) .............................................. 9900677

(51) Int. Cl.[7] ............................................ A61K 31/495
(52) U.S. Cl. ....................................................... 514/250
(58) Field of Search ........................................ 514/250

(56) References Cited

U.S. PATENT DOCUMENTS

| | | | |
|---|---|---|---|
| 5,866,575 A | * | 2/1999 | Bergman ..................... 514/250 |
| 6,239,133 B1 | * | 5/2001 | Barrish et al. ............... 514/250 |
| 6,248,742 B1 | * | 6/2001 | Bergman et al. ............ 514/250 |
| 6,258,357 B1 | * | 6/2001 | Spaner .................... 424/93.71 |
| 6,333,327 B2 | * | 12/2001 | Moller et al. ................ 514/250 |

FOREIGN PATENT DOCUMENTS

| | | | | |
|---|---|---|---|---|
| EP | 0 480 257 | | 4/1992 | |
| WO | 95/02323 | * | 1/1995 | ............ A01N/1/02 |
| WO | WO95/02323 | | 1/1995 | |
| WO | WO96/19996 | | 7/1996 | |
| WO | 96/19996 | * | 7/1996 | ......... A61K/31/485 |
| WO | WO97/24924 | | 7/1997 | |
| WO | 97/24924 | * | 7/1997 | ......... A61K/31/565 |

* cited by examiner

Primary Examiner—James H. Reamer
(74) Attorney, Agent, or Firm—Browdy and Neimark, P.L.L.C.

(57) ABSTRACT

Use of a compound of formula (I), wherein $R_1$ represents hydrogen or one or several, preferably 1 to 4, similar or different substituents in the positions 1–4 and/or 7–10, selected from halogen, preferably Br, lower alkyl/alkoxy group having not more than 4 carbon atoms, trifluoromethyl group, trichloromethyl group, trichloromethyl group; and in one of the positions 7–10 $R_1$ can be a hydroxyl group; X is a group—$(CH_2)n$—$R_2$, wherein $R_2$ represents a nitrogen containing basic residue such as $NH_2$, $NHR_4$ or $NR_5R_6$, wherein $R_4$, $R_5$ and $R_6$ independently are lower alkyl or cycloalkyl and n is an integer of from 1 to 4 and $R_3$ represents hydrogen, lower alkyl/cycloalkyl group having not more than 4 carbon atoms, and the physiologically acceptable addition products of the compounds with acids and halogen adducts, preferably adducts with iodine, iodine monochloride or iodine monobromide, as an agent for protecting tissues, organs and cells in transplantation is described.

12 Claims, 8 Drawing Sheets

ISCHEMIA FOR 10 MIN.

AGENT FOR USE IN TRANSPLANTATION

REFERENCE TO RELATED APPLICATIONS

The present application is the national stage under 35 U.S.C. 371 of international application PCT/SE00/00339, filed Feb. 18, 2000 which designated the United States, and which international application was published under PCT Article 21 (2) in the English language.

The present invention relates to an agent for use in transplanting a tissue or an organ from a donor to a receiver with the need of such an organ.

Transplantation of tissues (organs) is an area within the health care system undergoing a fast development and with an increasing number of transplants per year. There is definitely a very limited supply of tissues (organs) and the tissues (organs) are under normal circumstances available only a few hours before the transplantation. The limiting factor is the time that is available after the removal of the tissue(organ) from the donor and until it is function in the receiver of the tissue(organ). The time factor is thus very critical and requires night time operations (day time operations are not possible with a few hours notice), ambulance and air transportation and several ongoing operations to prepare the receivers which could be up to 5–6 different patients at different hospitals. The receiver operation can take up to 12 hours in the case of a liver transplantation.

In the following specification and the claims the term tissue is intended to comprise all tissues, organs and cells that can be transplanted. These terms are used interchangeably in this specification.

There are three problematic steps in transplantation, all involving potential problems of oxidative stress, i.e. the quality of the tissue (organ), i.e. survival.

I. The time at intensive care for the donor. This means exposure to oxygen (higher percentage and pressure) and failure of a number of normal body functions.

II. The time after the removal to the function in the receiver. This is very critical. The organ is chilled to +4° C. and washed with a solution for storage and transport, eg. a UW-solution. After the removal, the organ is stored in said solution on ice. UW-solution is saline with additions to maintain the salt-balance and avoid tissue damage.

III. In the receiver there are several critical steps, the first being re-perfusion, i.e. to turn on the blood flow again: Re-perfusion causes a massive oxidative burst. Secondly there are immune reactions and long-term effects of the transportation (partial cell death of certain groups of cells).

The optimization of the transplantation procedure is of great importance and several receivers life depends on that the whole procedure is very efficient and that the organs are not destroyed in this process.

Oxidative stress occurs when there is an imbalance between oxidants and free radicals versus protective mechanisms like SOD enzymes, catalase, DNA-repair etc. Oxidative stress is a major or minor part of most diseases, examples are: heart/brain infarctions, trauma, sepsis, arthritis, diseases of the immune system, cancer, inflammation, infection and CNS-diseases. In all these diseases the oxidative stress leads to cell damage and the outcome is dependent upon if the organ can survive the acute phase, a situation that is obvious during infarction but also relevant for chronic diseases like arthritis with a constant oxidative stress of the joints.

The present invention relates to the use of an agent in the transplantation of an organ from a donor to a receiver with the need of such an organ. The agent according to the present invention is suitable to use in different steps which are related to the transplantation procedure. Thus, the agent can be a) administered orally, intraperitoneally or intravenously to a donor from which an organ shall be removed; b) the agent can be added to a solution in which the organ is to be stored and transported (eg. a UW solution) c) the agent is administered orally, intraperitoneally or intravenously to the receiver of the organ, i.e. the patient in which the organ shall be implanted.

In tissue degradation several mechanisms are involved, since oxidative stress affects tissues by several different mechanisms, viz. by oxidation of proteins, lipids-and DNA. During the oxidation of proteins and lipids of the tissue all structures are severely damaged by free radicals a consequence of which is loss of function which leads to cell death and ultimately to the death of the tissue.

According to the present invention it has surprisingly been found that by using an agent, which is a substituted indoloquinoxaline of the following general formula I, the organ which is transplanted is protected against degradation caused by oxidative stress during the whole sequence of steps which are necessary for carrying out a transplantation.

The agent which according to the present invention is to be used in connection with the transplantation is a compound of the following general formula I wherein $R_1$ represents hydrogen or one or several, preferably 1 to 4, similar or different substituents in the positions 1–4 and/or 7–10, selected from halogen, preferably Br, lower alkyl/alkoxy group having not more than 4 carbon atoms, tri-fluoromethyl group, trichloromethyl group; and in one of the positions 7–10 $R_1$ can be a hydroxyl group;

X is a group—$(CH_2)n$—$R_2$, wherein $R_2$ represents a nitrogen containing basic residue such as $NH_2$, $NHR_4$ or $NR_5R_6$, wherein $R_4$, $R_5$ and $R_6$ independently are lower alkyl or cycloalkyl and n is an integer of from 1 to 4 and $R_3$ represents hydrogen, lower alkyl/cycloalkyl group having not more than 4 carbon atoms, and the physiologically acceptable addition products of the compounds with acids and halogen adducts, preferably adducts with iodine, iodine monochloride or iodine monobromide.

$R_1$ is preferably selected from hydrogen and lower alkyl groups, especially methyl. More preferably $R_1$ is methyl in positions 2 and 3 and hydrogen in the other positions.

A compound which proven to be especially effective is the compound of the following formula II Such compounds and their preparation are described in EP patent 0238459 and U.S. Pat. No. 4,990,510 which are incorporated herein by reference.

The use of the agent according to the present invention in these three applications[I, II and III)] is prophylactic for preventing tissue damages during the transplantation. Thus, by treating the tissue which shall be transplanted in situ the protective mechanisms are activated which secure the survival of the organ. The agent according to the present invention thus, acts so that the tissue degradation mechanisms are down-regulated/blocked which means that the period for storage and transport of the tissue is prolonged. This extension of time means that a higher number of countries and regions can be involved in the exchange of tissues for transplantation. Thus,when tissues are transplanted they are submitted to tissue degradation if not the DNA/protein/enzymes etc. of the tissues are protected against degradation.

General tissue damage can be measured by means of measuring metabolic capacity or tissue function. Thus, for a tissue like the liver the capacity to reduce lactate levels of the blood and produce bile are such markers(indicators). Since DNA controls the whole function of the cell and thereby the whole tissue, oxidation of DNA is also a risk factor for survival. Oxidation of DNA is also a promutagenic event.

In the DNA oxidation cells are exposed to reactive oxygen. During this oxidative stress hydroxyl and superoxide radicals oxidize dG which leads to 8-OH-dG formation which is a promutagenic event which leads to strand breaks, base-substitutions, ring opening of dG and/or affects DNA-methylation. (dG is deoxyguanosine, one of the bases of DNA).

The agent of formula I represents a potentially important agent to increase the survival of cells and organs during transplantation by dramatically reducing the oxidative stress. The agent of formula I is a non-toxic substance in vivo and protects the tissues in two ways. First there is a blocking of oxidative enzymes (oxidases) that generate oxidants. Secondly there is a gene-regulation that activates the general cell-defense. Thus, the agent of formula I does not work as an anti-oxidant but activates the defense mechanisms of the cell to up-regulate the protection for oxidative stress.

In the enclosed drawings

In order to investigate the agents to be used in transplantation according to the present invention a liver from rat was tested in a perfusion solution in a heart/lung machine. In order to measure organ damage the amount of 8-OH-dG in the liver was analysed. As an inducer of 8-OH-dG dimethylsulphoxide (DMSO) was added to a perfusion solution. (DMSO is a known compound that affects cell membranes). In the experiment different test groups were used, a control group of livers, designated controls C, without any addition to the perfusion solution, one group to which 100 $\mu$l of DMSO was added to the perfusion solution, which resulted in a significant increase of 8-OH-dG, and three different groups to which a compound to be used according to the present invention (B220) was added in a dosage of 2, 5 and 10 mg, respectively before the addition of 100 $\mu$l of DMSO. The results of the test can be seen from FIG. 1 of the drawings.

Figure 1:
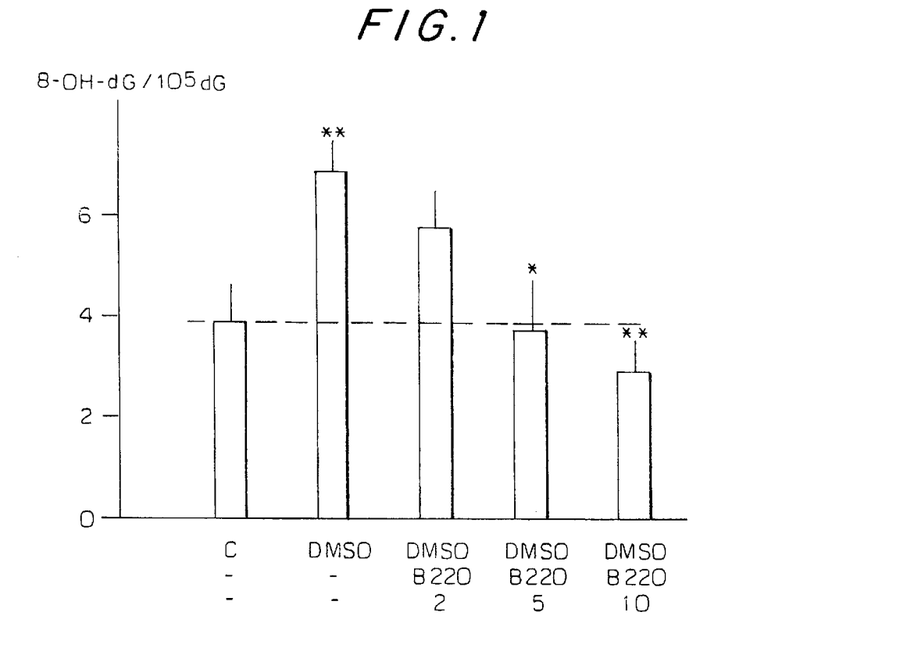
FIG. 1 illustrates oxidative lesions of DNA (8-OH-dG) in a liver perfusion system.

From said figure it can be seen that B220 protects against oxidation of DNA in a dose/response manner. Furthermore, it can be seen that B220 can reduce 8-OH-dG to below the control values, (down-regulation).

Figure 2:
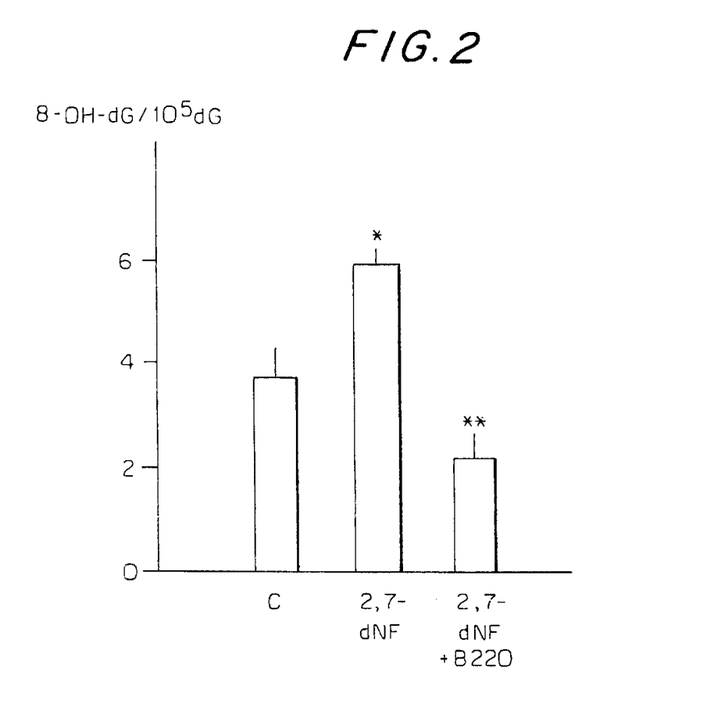
FIG. 2 illustrates in vivo test of rat livers with analysis of 8-OH-dG.

In another experiment rats were tested in vivo and the livers analyzed for 8-OH-dG. In this experiment there were three test groups. One control group, one group to which 2,7-dinitrofluorene (2,7-dNF), which is a well-known carcinogen found in diesel exhaust and inducer of 8-OH-dG, was orally administered and one group to which both 2,7-dNF and a compound to be used as an agent according to the present invention (B220) were administered. B220 was administered at three time points in relation to the 2,7-dNF dose, viz. −48 h, −24 h and +6 h. All doses were administered orally with the substance in corn oil. Control only received carrier. Oxidation of DNA (oxidation of guanine, 8-OH-dG) was measured in the liver. 8-OH-dG is a promutagenic event correlated to several different types of diseases, for instance cancer, diabetes and infectious diseases.

The results of the experiment can be seen from the enclosed FIG. 2. From said figure it can be seen that B220 does not only protects against 2,7-dNF-induced formation of 8-OH-dG but also reduces 8-OH-dG to below the control values (down-regulation).

Figure 3:
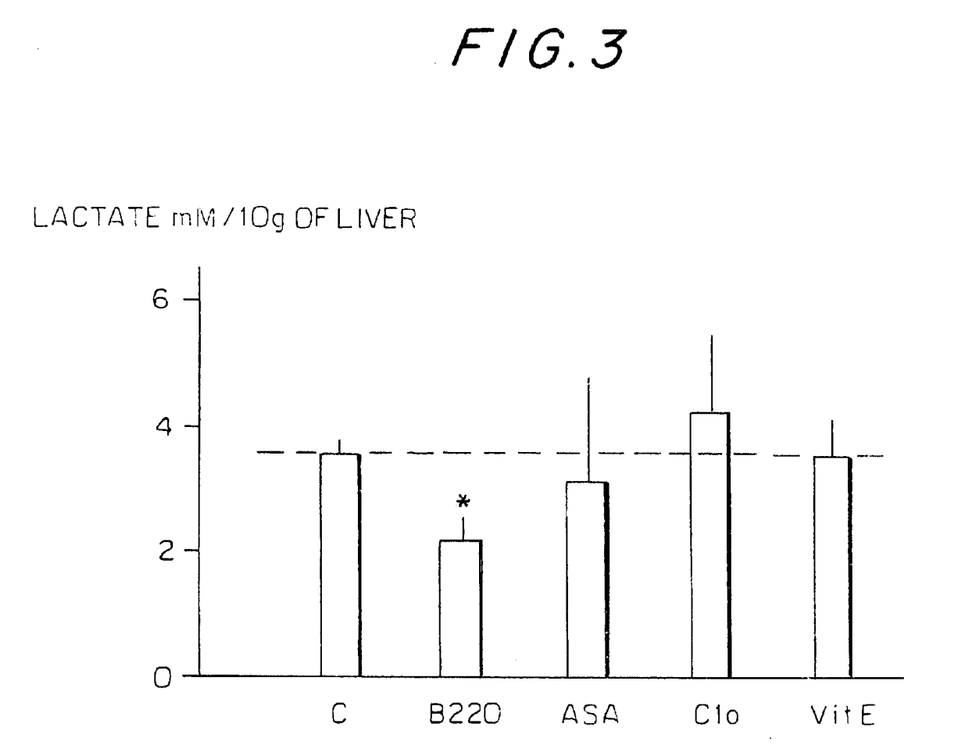
FIG. 3 illustrates inducement of ischemia in a liver perfusion system and reduction of lactate.

A third experiment was carried out, wherein rat livers were taken out and were subjected to perfusion in a heart/lung machine. The perfusion solution is blood with an implanted liver. When the system has reached equilibrium the perfusion flow is shut off and 10 to 20 minutes later the perfusion flow is turned on again, which is called reperfusion (ischemia). A known toxic effect of reperfusion (ischemia/infarction)(tissue damage due to oxidative stress) is the reduced capacity to remove lactate from the perfusate. In this experiment an agent to be used in transplantation according to the present invention (B220) was tested in comparison with three different compounds known to protect tissues, viz. acetyl salicylic acid (ASA, a well-known protection agent for inflammatory damage and fever), Clomethiasol (a new potential drug for treatment of brain damage due to brain infarction) and Vitamin E (a well-known anti-oxidant, scavenger for free radicals. In the controls(C) only ischemia was induced. In the other four groups the indicated substances were added (5 mg) to the perfusate before ischemia. B220 was the only substance that gave a significant reduction of lactate. ASA which is known to down regulate effects related to fever, inflammation and pain did not give any protective effects. The same was seen for Clomethiazol (a drug for protection of brain tissue after infarction), and vitamin E, a well-known antioxidant and tissue protective substance.

The result of said tests are illustrated in FIG. 3. From said figure it can be seen that B220 was the only substance of the tested ones which gave a statistically significant protection.

Figure 4A:
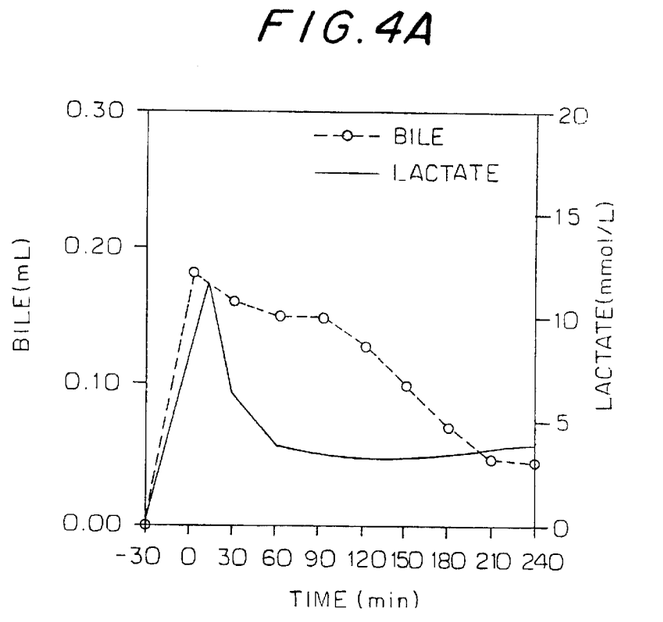
FIGS. 4 and 5 illustrate lactate and bile flow of rat livers in perfusion systems.
Figure 4B:
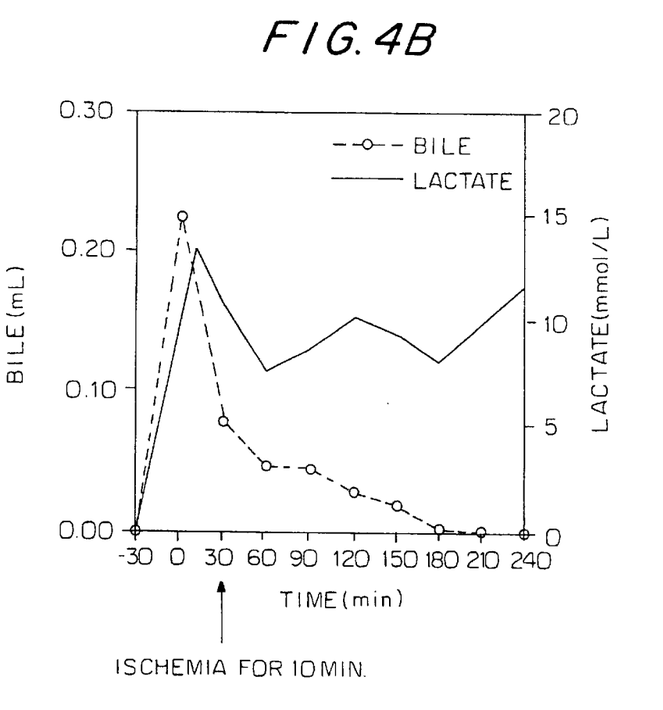
Figure 4C:
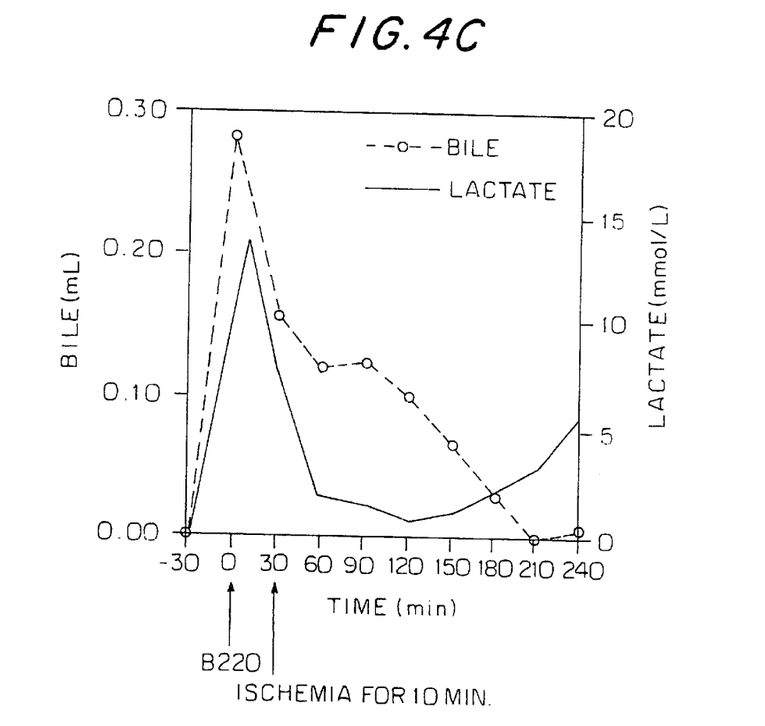
Figure 5A:
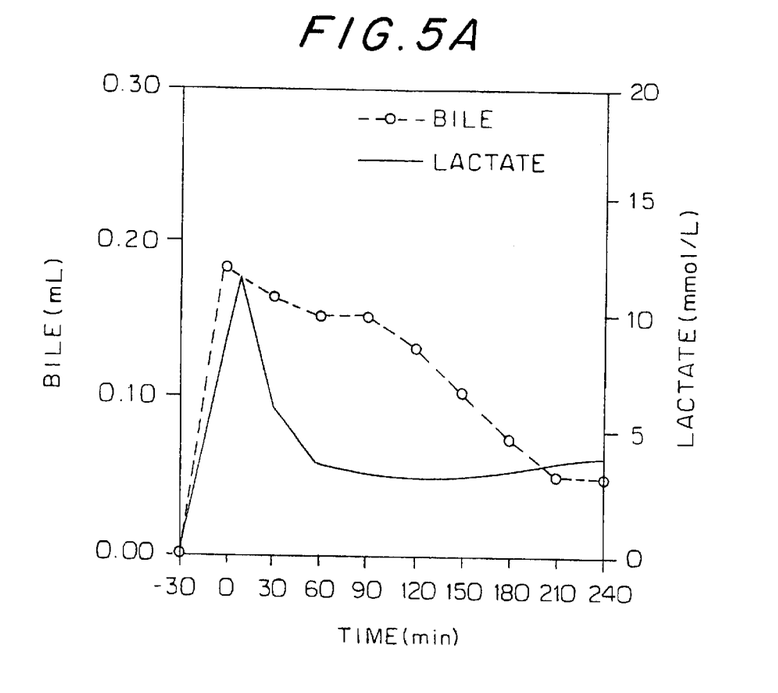
Figure 5B:
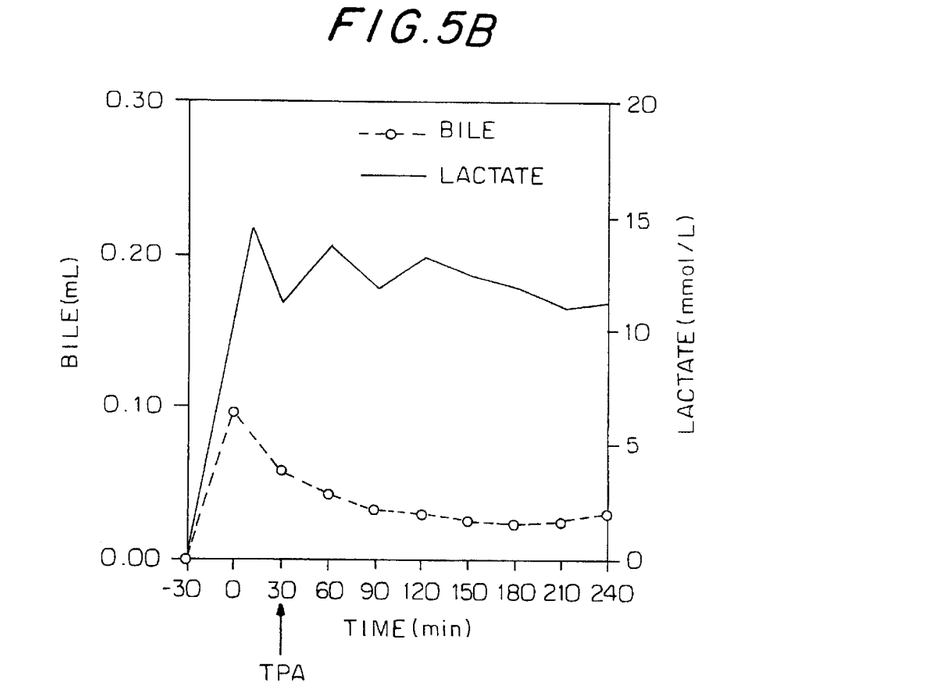
Figure 5C:
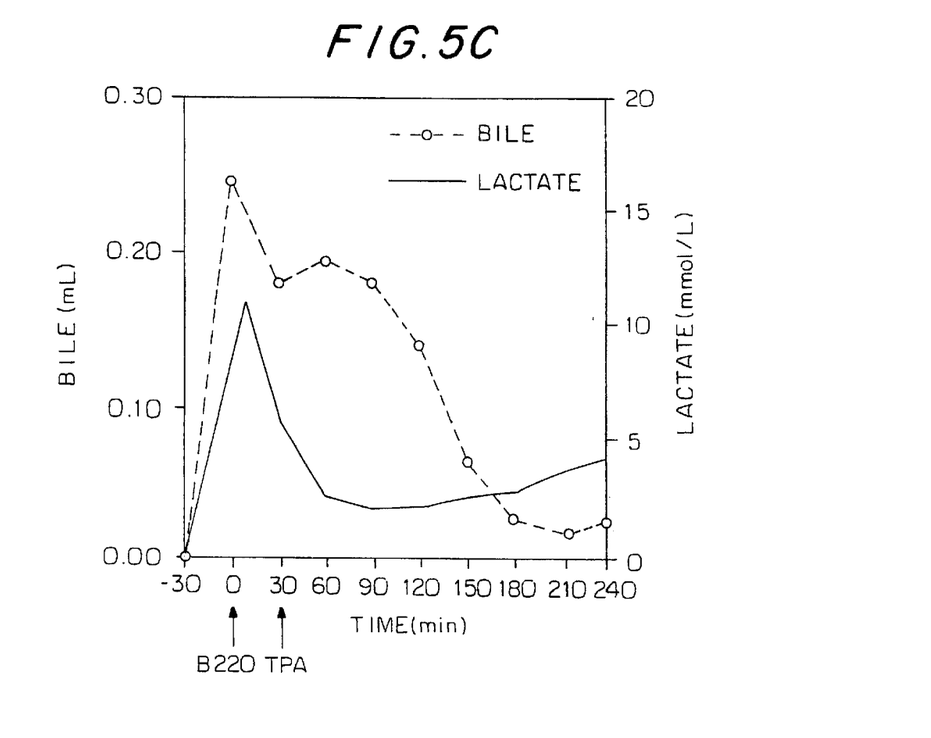

A series of experiments were carried out with rat livers in a heart/lung machine (FIGS. 4 and 5).

Lactate was added to a control liver perfusion and the bile flow and the lactate level were measured as a function of time. Bile flow is the clinical parameter for liver function, the higher bile flow the better liver function. The results from controls are shown in the upper diagrams of FIGS. 4 and 5. A normal liver down-regulates the lactate very rapidly to in vivo levels (3–5 mM). The normal bile flow in controls is represented by the dotted line.

In the next experiment a heart/lung machine was shut off for 10 minutes and then it was started again to induce oxidative stress (reperfusion). The amount of lactate, which is a measurement of tissue damage, was determined as a function of time and the bile flow as a function of time was also determined as an indicator of toxic effect. The results are shown in FIG. 4, middle diagram, indicating a high level of lactate (solid curve) and a reduced bile flow (dotted curve) after reperfusion. Both these effects are markers for tissue damage.

In the next experiment the same reperfusion experiment was carried out with B220 present in the system in an amount of 2 mg. The results in form of lactate amounts and bile flow are shown in FIG. 4 lower diagram. As can be seen from the results in FIG. 4 the amount of lactate and the bile flow rapidly accommodate to normal values, which indicated that B220 eliminates tissue damage of the liver caused by reperfusion. Both lactate removal and bile flow were better than in the controls.

In the next experiment (FIG. 5) a very toxic compound, triphorbolester (TPA) was added to the perfusion fluid. TPA is an inducer of inflammation and a very potent tumour promoter. The results as to lactate amounts and bile flow are shown in FIG. 5, middle diagram, indicating a very limited capacity to reduce lactate and a very restricted capacity to produce bile.

Then the same experiment was repeated under the same conditions except that 2 mg B220 also was added to the perfusion. The results are shown in FIG. 5, lower diagram. From said results it can be seen that when B220 is present in the system the toxic effects of TPA were prevented and the values of lactate and bile flow were restored (and even better as compared to the controls in FIG. 5, upper diagram). These data are relevant to the fact that B220 in vivo in long time experiments can stop the very potent tumour promoter effect of TPA (the most potent tumour promoter which is known in animal experiments) and "shut off" the tumour process. The mode of action resides in a blocking of hyperplasia/inflammation.

Figure 6:
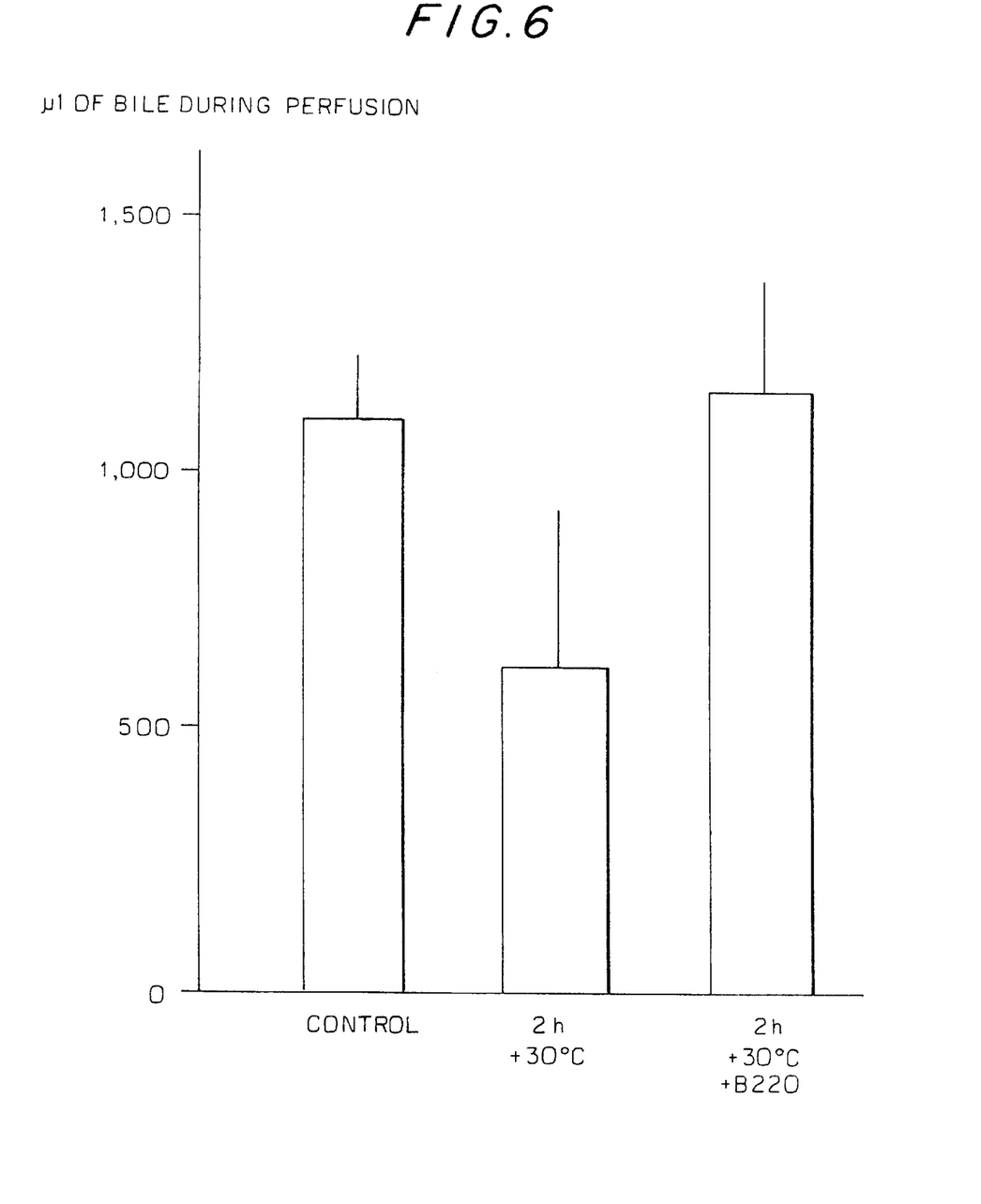
FIGS. 6 and 7 illustrate total bile flow of rat livers in perfusion systems.

In a further experiment rat liver was tested in isolated perfusion where B220 was administered to the donor. The donors were administered a single dose of B220 24 h before the livers were surgically removed and kept at +30° C. for 2 h before set into perfusion (group 3). (There was a "short" storage (2 h) of rat liver at a high temperature (+30° C.) in order to simulate transplantation). The second group was not administered B220 and the first group was controls directly set into perfusion. With a dose of B220 (i.p. 24 h prior to surgery) to the donor the toxic effects are eliminated measured as total bile flow during the perfusion. "Transport" and reperfusion gives a massive oxidative stress which leads to tissue damage.

In FIG. 6 the total bile flow was an indicator of tissue damage induced by transplantation. The controls were directly "transplanted" to the perfusion system while the second group of livers was kept for 2 h at 30° C. before "transplantation". The third group represents the 2 h at 30° C. treatment but with addition of B220 to the donors. From the figure it can be seen that B220 completely restored the bile flow value to that of the control samples.

Figure 7:
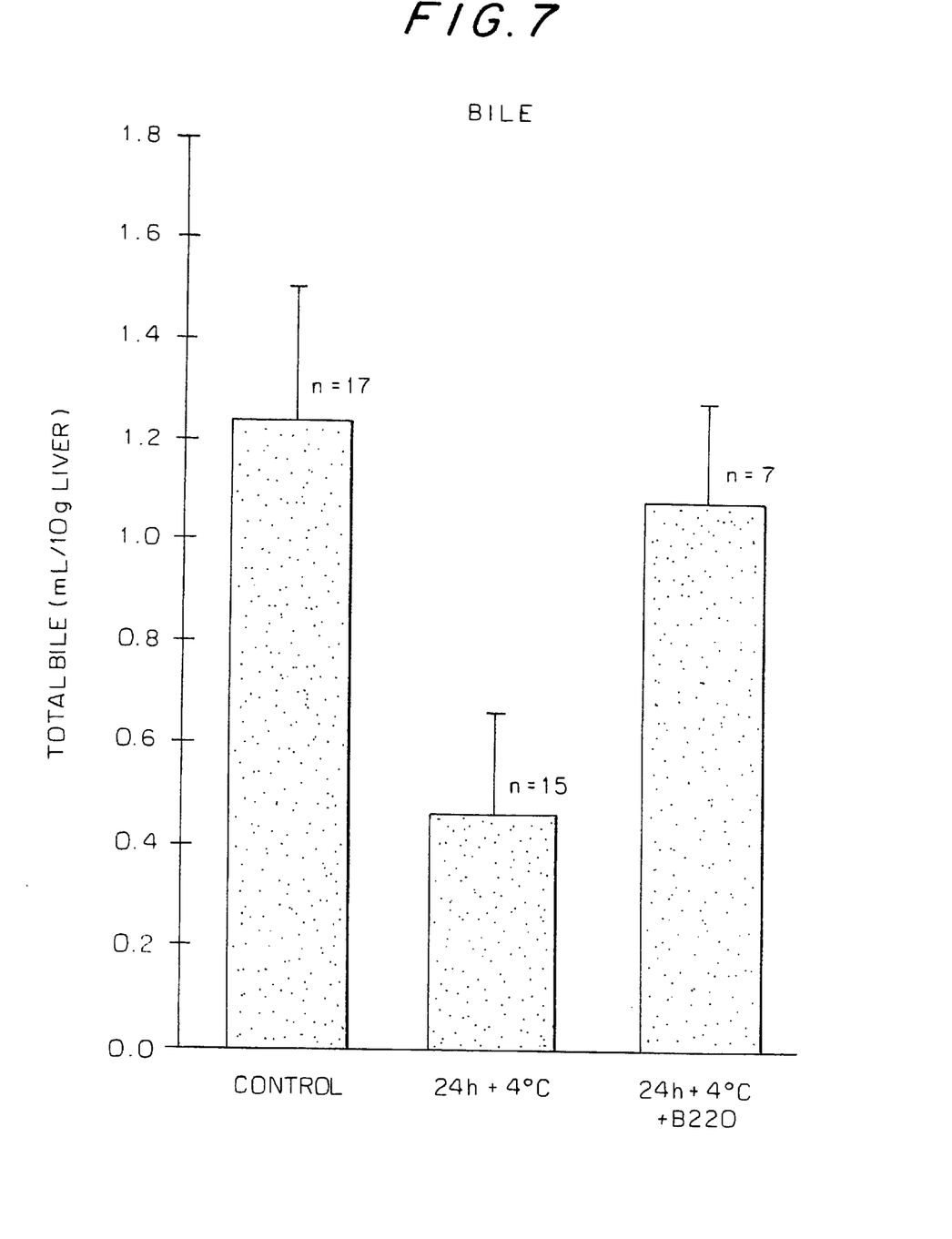
Figure 8:
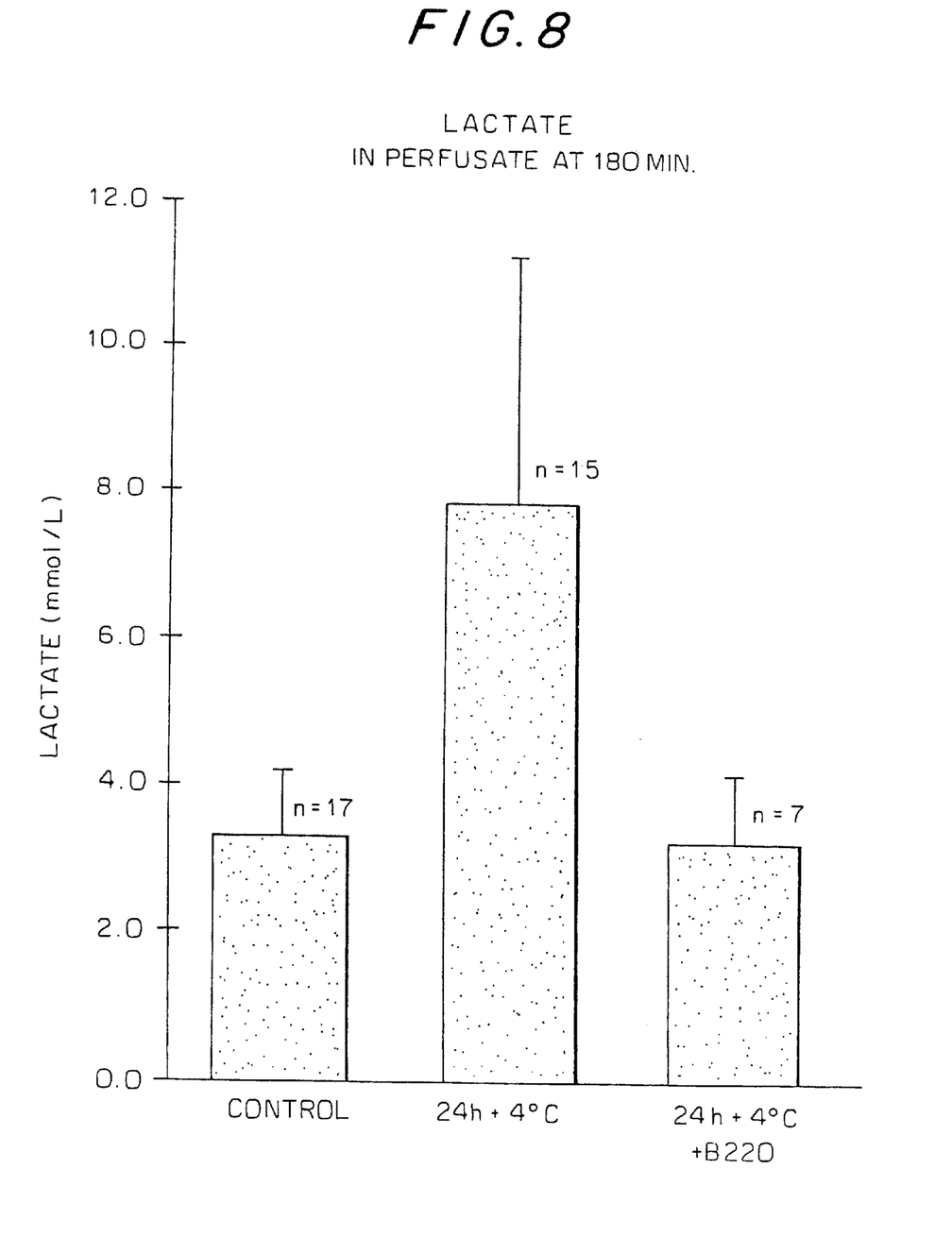
FIG. 8 illustrates the lactate levels of rat liver in a perfusion system.

The same experiment was repeated but instead the temperature applied during transport of human livers(+4° C.) was used. The livers were stored for 24 h before installation in the perfusion system. This should be compared to 12 h which is the maximum for human liver transplantation. As can be seen in FIG. 7 the bile flow was restored with pretreatment of B220 to the donor. FIG. 8 shows the same protective effect on lactate levels. The experiment was identical to what is shown in FIG. 6 except for time and temperature used.

The experiments show that the agent of formula I protects the liver under circumstances which are applied for human liver transplantation. This means that the agent can function at storage temperatures(+4° C.) and transportation times used in human liver transplantation. The protective effect of the agent can be achieved by intraperitoneal, oral or intravenous administration. The time for pretreatment can be reduced if that time is not available in the acute situation. In addition the time for transportation between a donor and a receiver can most likely be prolonged to 24 h compared to the today maximum of 12 h.

From the above examples it can be seen that pre-treatment with B220 to the donor in case of transplantation effectively down-regulates the oxidative stress. This down-regulation does not only eliminate the oxidative stress caused by the transportation but even down-regulates the oxidative stress to levels below the control values. This effect in combination with a very low toxicity (practically non-toxic) suggests that B220 interfere with the normal regulation (protection) of oxidative stress. In addition, the lipophilic character of B220 enables rapid absorption via cell membranes.

The consequence, in terms of transplantation, is that there is a prolonged survival of the tissues i.e. that longer transportation and storage will be possible (higher numbers of organs will be available for transplantation) and that the chances for survival and function of the organ increases.

What is claimed is:

1. A method for protecting at least one of (1) tissues, (2) an organ and (3) cells in transplantation from a donor to a receiver, comprising administering a protective compound to said donor or to said receiver, wherein said compound is a compound which is a substituted indoloquinoxaline of the formula I wherein R₁ represents hydrogen or at least one substituent in the positions 1–4 and/or 7–10 selected from the group consisting of halogen, lower alkyl/alkoxy group having not more than 4 carbon atoms, trifluoromethyl group, trichloromethyl group; and in one of the positions 7–10 R₁, is optionally a hydroxyl group;

X is a group—$(CH_2)_n$—$R_2$, wherein $R_2$ represents a nitrogen containing basic residue, and n is an integer of from 1 to 4, and $R_3$ represents hydrogen, lower alkyl/cycloalkyl group having not more than 4 carbon atoms, or a physiologically acceptable additions product of said compound with an acid or halogen adduct; or storing at least one of said tissues, said organ or said cells for transplantation in a solution of said compound.

2. The method according to claim 1 wherein $R_1$ is methyl in positions 2 and 3 and hydrogen in the other positions.

3. The method according to claim 1 or 2 wherein $R_1$ in one of the positions 7–10 is hydroxy.

4. The method according to claim 1 or 2 wherein X is $CH_2N(CH_3)_2$ and $R_3$ is hydrogen.

5. The method according to claim 1 or 2 wherein the compound is added to a solution in which the organ to be transplanted is to be stored and transported.

6. The method according to claim 1 or 2 wherein the compound is added to a perfusion system in connection with the transplantation.

7. The method according to claim 1 or 2 wherein the compound is injected or administered to a donor from which the tissue is to be removed.

8. The method according to claim 1 or 2 wherein the compound is administered to a receiver of the tissue which is to be transplanted.

9. The method of claim 1 wherein said halogen is Br.

10. The method of claim 1 wherein $R_2$ is $NH_2$, $NHR_4$ or $NR_5R_6$, wherein $R_4$, $R_5$ and $R_6$ independently are lower alkyl/cycloalkyl.

11. The method of claim 1 wherein said compound is an adduct with iodine, iodine monochloride or iodine monobromide.

12. The method of claim 3 wherein said hydroxy is at position 9.

* * * * *